United States Patent
Ricard et al.

(10) Patent No.: US 8,679,846 B2
(45) Date of Patent: Mar. 25, 2014

(54) STERILISATION INDICATOR

(75) Inventors: André Ricard, Toulouse (FR); Francis Dieras, Bordeaux (FR); Michel Sixou, Balma (FR); Sandrine Villeger, Toulouse (FR); Cristina Canal, Barcelona (ES); Pilar Erra, Barcelona (ES)

(73) Assignee: Societe pour la Conception des Applications des Techniques Electroniques, Merignac (FR)

( * ) Notice: Subject to any disclaimer, the term of this patent is extended or adjusted under 35 U.S.C. 154(b) by 35 days.

(21) Appl. No.: 12/519,433

(22) PCT Filed: Dec. 20, 2007

(86) PCT No.: PCT/FR2007/052573
§ 371 (c)(1),
(2), (4) Date: Jun. 16, 2009

(87) PCT Pub. No.: WO2008/078053
PCT Pub. Date: Jul. 3, 2008

(65) Prior Publication Data
US 2010/0107962 A1    May 6, 2010

(30) Foreign Application Priority Data
Dec. 22, 2006 (FR) ...................... 06 11334

(51) Int. Cl.
*G01N 33/00* (2006.01)
(52) U.S. Cl.
USPC ............ 436/1; 436/164; 436/147; 436/127; 436/106; 422/28; 422/1; 422/83; 422/86

(58) Field of Classification Search
USPC ............ 436/164, 147, 127, 106, 1; 422/28, 1, 422/83, 86
See application file for complete search history.

(56) References Cited

U.S. PATENT DOCUMENTS

| | | | |
|---|---|---|---|
| 3,738,811 A | 6/1973 | Cheng | |
| 4,188,437 A | 2/1980 | Rohowetz | |
| 4,436,819 A | 3/1984 | Manning | |
| 5,340,537 A | 8/1994 | Barrett | |
| 5,482,684 A | 1/1996 | Martens et al. | |
| 6,267,242 B1 | 7/2001 | Nagata | |
| 6,488,890 B1* | 12/2002 | Kirckof | 422/403 |
| 6,659,036 B2 | 12/2003 | Omatsu | |
| 7,718,433 B2* | 5/2010 | Stecklein et al. | 436/10 |

(Continued)

FOREIGN PATENT DOCUMENTS

| | | |
|---|---|---|
| FR | 2856600 A1 | 12/2004 |
| FR | 2879933 A1 | 6/2006 |

(Continued)

OTHER PUBLICATIONS

International Search Report dated Nov. 4, 2008 established in International Application No. PCT/FR2007/052573.

(Continued)

*Primary Examiner* — Monique Cole
(74) *Attorney, Agent, or Firm* — Workman Nydegger

(57) ABSTRACT

The invention provides a sterilization indicator (17), characterized in that it comprises:
  a compound (21) that is of the heating type when put into contact with atoms of oxygen O and/or nitrogen N; and
  a thermochromic dye (19), in thermal contact with the compound (21).

11 Claims, 1 Drawing Sheet

(56) References Cited

U.S. PATENT DOCUMENTS

| | | | |
|---|---|---|---|
| 2001/0054374 A1 | 12/2001 | Omatsu et al. | |
| 2003/0072674 A1* | 4/2003 | Melker et al. | 422/21 |
| 2003/0211618 A1* | 11/2003 | Patel | 436/38 |
| 2006/0083657 A1 | 4/2006 | McDonnell | |

FOREIGN PATENT DOCUMENTS

| | | | |
|---|---|---|---|
| JP | 2004298479 A | 10/2004 | |
| JP | 2005111154 A | 4/2005 | |
| WO | 0072889 A1 | 12/2000 | |
| WO | 03037391 A1 | 5/2003 | |

OTHER PUBLICATIONS

Supplemental International Search Report in International Application No. PCT/FR2007/052573, Sep. 1, 2010.

Moreau S et al, "Using the Flowing Afterglow of a Plasma to Inactivate *Bacillus subtilis* Spores: Influence of the Operating Conditions", Journal of Applied Physics, American Institute of Physics, Jul. 15, 2000, pp. 1166-1174, vol. 88, No. 2, New York, US. (XP012051169).

* cited by examiner

STERILISATION INDICATOR

FIELD OF THE INVENTION

The present invention relates to a sterilization indicator, usable in particular for sterilizing medical or surgical instruments, in particular for dental use, by means of a post-discharge plasma obtained from a gas based on nitrogen and/or oxygen.

BACKGROUND

Sterilization consists in destroying a significant number, in a given proportion, of microorganisms, viruses, or pathogenic proteins present on the inside or outside surfaces of articles to be sterilized.

It should be observed that the adjective "sterile" is an absolute term, whereas ensuring that an article is sterile, i.e. free from microorganisms, is a probability function. The sterility assurance level (SAL) of an article is defined as the probability that any given unit is not sterile after being exposed to a validated sterilization process. Thus, for an article to be considered as being sterile with respect to European standard EN556, it must possess an SAL of $10^{-6}$, i.e. the theoretical probability of isolating a microorganism must be less than 1 in $10^6$.

Various sterilization processes are known, including chemical and physical processes.

Amongst chemical sterilization processes, these sterilization processes use gases such as ethylene oxide, formaldehyde, or hydrogen peroxide. Those processes nevertheless present the drawback of requiring a long period of time for desorption, and that is incompatible with the instruments for sterilizing being made rapidly available. In addition, those gases are toxic and irritate the skin and the mucous membranes.

Physical processes include in particular steam sterilization in an autoclave under the action of temperature and steam; dry hot sterilization; radiation using ion beams or gamma rays, used on articles that cannot be sterilized by means of heat or chemically; or indeed filtering using filters that are suitable for separating out microorganisms. Those processes generally involve high temperatures, often higher than 100° C.

Because of the increasing use in medical articles of materials that are temperature-sensitive, such as polymer-based materials, it is desirable to develop sterilization processes usable at low temperature, and in particular at temperatures lower than 70° C.

Sterilization processes have thus been developed that makes use of a plasma, operating at temperatures that makes it possible to avoid damaging temperature-sensitive materials.

For example, application WO 00/72889 discloses a sterilization process that uses a plasma based on oxygen and nitrogen. Application FR 2 856 600 describes a sterilization process making use of a post-discharge plasma coming from a plasma made exclusively of nitrogen, while application FR 2 879 933 uses a post-discharge plasma coming from a plasma made up of hydrogen and of nitrogen. Numerous sterilization processes thus make use of a gas based on nitrogen or oxygen for preparing the plasma.

In order to validate sterilizers, use is made of sterilization indicators that make it possible to monitor one or more essential parameters of the sterilization process. For this purpose, three types of sterilization indicator have been developed: physical, chemical, and biological indicators.

Sterilization indicators for processes making use of a plasma are still little developed. Documents U.S. Pat. No. 6,659,036, WO 98/46279, JP 2005111154, and JP 2004298479 disclose sterilization indicators relating to processes that make use of plasma. Nevertheless, those documents do not relate to plasmas based on nitrogen and/or oxygen.

It thus appears necessary to have sterilization indicators available that enable at least one parameter of the sterilization process to be evaluated for sterilization processes making use of a post-discharge plasma obtained from a gas comprising nitrogen $N_2$ and/or oxygen $O_2$.

SUMMARY

The Applicant has developed a sterilization indicator enabling this objective to be achieved. In particular, the indicator of the invention enables the presence of atoms of oxygen O and/or nitrogen N to be indicated in a post-discharge plasma.

The sterilization indicator of the invention, usable in a sterilization device, comprises:
  a compound of the type that heats on being put into contact with atoms of oxygen O and/or nitrogen N, in particular those present in a post-discharge plasma obtained from a gas comprising oxygen $O_2$ and/or nitrogen $N_2$; and
  a thermochromic dye, in thermal contact with the compound.

The term "in thermal contact with the compound" in the meaning of the invention designates a dye that is placed relative to the compound in such a manner that heating of the compound causes the temperature of the dye to rise.

The compound is preferably in the form of a powder, particles, filaments, or fibers, in order to ensure a large contact area between the compound and the dye, thereby enhancing heat exchange.

The compound preferably comprises at least one metal. Surface recombination of atoms of nitrogen N or hydrogen H, which is exothermal, is enhanced by the presence of metal surfaces. The probability of atomic recombination of atoms of nitrogen N or oxygen O is large on metal surfaces. Since this reaction is exothermal, the reaction energy of the recombination is transferred in part to the metal.

The metal of the compound may be selected from copper, titanium, steels, aluminum, and alloys thereof.

It is preferable to use copper and its alloys.

The thermochromic dye may be reversible or irreversible. A thermochromic dye is a dye that changes color under the action of temperature. It is irreversible when the color obtained under the action of temperature is permanent over time and does not return to its original color.

The reversible or irreversible nature of the thermochromic dye is selected as a function of the use intended for the indicator. If it is desired to track changes in the color of the dye in real time and to make use of it again quickly after sterilization, then a reversible thermochromic dye can be used. In contrast, if the indicator is to be stored with the articles for sterilization for the purpose of subsequent verification of sterilization parameters, then irreversible thermochromic dye should be used.

The dye should be selected as a function of the nature of the compound and of the parameters of the sterilization process. The temperature rise of the dye is a function of the capacity of the compound to heat up in contact with atoms of nitrogen N and/or oxygen O, and also of the quantity of atoms of nitrogen N and/or oxygen O with which the compound is put into contact.

The compound and the dye are preferably in contact with a medium, i.e. disposed on and/or in the medium. The compound may thus be disposed or dispersed on a medium on which the dye is disposed. The compound may also be disposed inside the medium, e.g. by spraying or by interlacing in the form of fibers in the medium.

Any type of medium may be used, e.g. a medium that is porous, in order to facilitate diffusion of the dye in the medium.

The medium may be in the form of a plate, e.g. made of polymer or of metal, in the form of fibers, e.g. metal, natural, or chemical fibers, or indeed in the form of woven or non-woven fabrics.

In particular, the medium may be selected from cellulose, fabric, fibers, cotton, paper, and blotting paper.

The invention also provides a method of indicating the presence of atoms of oxygen O and/or nitrogen N in a plasma present in a post-discharge chamber (post-discharge plasma). The method is advantageously implemented in a post-discharge chamber of a sterilization device using a plasma obtained from a gas comprising oxygen $O_2$ and/or nitrogen $N_2$. The method comprises in succession:

putting a sterilization indicator of the invention into contact with the plasma; and comparing the color of the dye of the indicator with a reference color.

The reference color is set as a function of parameters used during the sterilization process.

Thus, by comparing the color of the dye after the process with the reference color, it is possible to observe whether the indicator of the invention has been subjected to the desired quantity of atoms of nitrogen N and/or oxygen O. The heating of the compound, and thus its temperature, are proportional to the quantity of atoms of nitrogen N and/or oxygen O with which the compound is in contact. Since the temperature reached by the compound determines the color of the dye, the color observed is indeed associated with the quantity of atoms of nitrogen N and/or oxygen O with which the compound has been in contact.

The color of the indicator of the invention can be compared with the reference indicator visually or by using automatic comparator means, such as a spectrophotometer, for example.

In order to define whether two colors are considered to be identical, it is possible to use the Kubelka-Munk equation and color variation in accordance with the CIE Lab model a model for representing colors as developed by the International Commission on Illumination (CIE).

From the Kubelka-Munk equation, the ratio between the absorption coefficient K of the dye and the diffusion coefficient S of the dye is associated with the reflection coefficient β as follows:

$$K/S = (1-\beta)^2/(2\beta)$$

According to the CIE Lab model, the color difference between two compounds 1 and 2 is as follows:

$$\Delta E^*_{ab} = ((L^*_2 - L^*_1)^2 + (a^*_2 - a^*_1)^2 + (b^*_2 - b^*_1)^2)^{1/2}$$
$$= (\Delta L^{*2} + Da^{*2} + Db^{*2})^{1/2}$$

in which equation, L* is luminance, a* represents position on the magenta->green axis, and b* represents position on the yellow->blue axis.

For the colors of two dyes to be considered as being identical, it is thus possible to require $\Delta E^*_{ab} \leq 2$.

In one implementation, the indicator can also be used to indicate temperature in the post-discharge chamber. Under such circumstances, it is appropriate to observe the color of the dye when the indicator is placed in the post-discharge chamber, at the beginning of the sterilization process. The heating of the compound under the effect of contact with atoms of nitrogen and/or oxygen is slower than the change in the color of the dye associated with the temperature that exists in the post-discharge chamber.

In this implementation, it is preferable to select a thermochromic dye in which color change is progressive as temperature goes from ambient temperature (20° C.) to the temperature to which the metal is heated, so as to present at least two distinct colors.

Such a dye may in particular be a dye from Chemsong Inc.

The invention thus provides a method of indicating a) the presence of atoms of oxygen O and/or nitrogen N in a plasma present in a post-discharge chamber, possibly being obtained from a gas comprising oxygen $O_2$ and/or nitrogen $N_2$; and b) the temperature in the post-discharge chamber.

The method comprises in succession:

putting a sterilization indicator of the invention into contact with the plasma;

comparing the color of the dye of the indicator with a first reference color, characteristic of a reference temperature in the chamber; and comparing the color of the dye of the indicator with a second reference color, characteristic of a reference quantity of atoms of oxygen O and/or nitrogen N.

It is thus possible to compare the color of the dye at the beginning of sterilization with a first reference color in order to ensure that the reference temperature in the post-discharge chamber has been reached. The color of the dye is also compared at the end of sterilization with a second reference color, in order to ensure that the reference quantity of atoms of nitrogen N and/or oxygen O that have come into contact with the indicator is reached during the sterilization process.

The invention also provides a sterilization indicator enabling verification of the temperature in the post-discharge chamber to be simplified, while also making it possible to verify the presence of atoms of nitrogen N and/or oxygen O in the post-discharge chamber. This indicator comprises:

a first portion, comprising a compound of the heating type on being put into contact with atoms of oxygen O and/or nitrogen N, and a thermochromic dye in thermal contact with the compound; and a second portion, comprising a thermochromic dye, and not including a compound of the heating type when put into contact with atoms of oxygen O and/or nitrogen N.

The first portion is identical to the above-described indicator and serves to verify the content in atoms of nitrogen N and/or oxygen O in the post-discharge plasma.

The second portion comprises a thermochromic dye, but does not include a compound of the heating type. The second portion of the sterilization indicator serves to verify the temperature that exists inside the post-discharge chamber (the sterilization chamber). The dye is not in contact with the heating compound, and it is subjected only to the temperature of the post-discharge chamber, without any other heating.

The dye of the second portion of the indicator may be the same dye as that present in the first portion.

The invention thus provides a method of indicating: a) the presence of atoms of oxygen O and/or nitrogen N in a plasma present in a post-discharge chamber, in particular obtained from a gas containing oxygen $O_2$ and/or nitrogen $N_2$; and b)

the temperature in the post-discharge chamber. The method comprises in succession:

putting said sterilization indicator into contact with the plasma; and comparing the colors of the dyes of the first and second portions of the indicator with two reference colors.

The color of the dye of the first portion of the indicator can be compared with the first reference color, characteristic of a reference quantity of atoms of oxygen O and/or nitrogen N, and then the color of the dye of the second portion of the indicator can be compared with the second reference color, characteristic of a reference temperature in the chamber. It is also possible to compare the colors of the two portions with each other.

By using the two-portion indicator, there is no longer any need to track changes in the method in real time.

Other objects, characteristics, and advantages of the invention appear on reading the following description given purely by way of example, and made with reference to the accompanying drawing, in which:

DETAILED DESCRIPTION OF VARIOUS EMBODIMENTS OF THE DISCLOSURE

Figure 1:
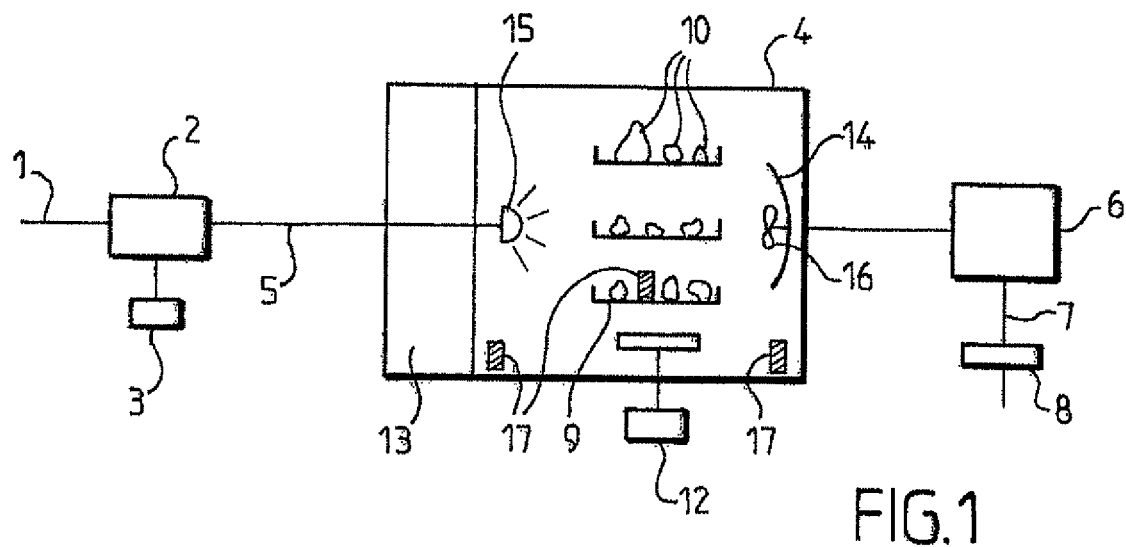
FIG. 1 is a diagram showing a sterilization device with an indicator of the invention.

The sterilization device as shown in FIG. 1 comprises an inlet pipe 1 for a stream of nitrogen $N_2$ that passes through an evacuated enclosure 2 subjected to an electric field produced by a microwave generator 3 operating at 2.45 gigahertz (GHz). The electric field serves in particular to form atoms of N from the molecules of $N_2$. The plasma as produced in this way is conveyed to a sterilization chamber 4 via a pipe 5, with the help of a vacuum pump 6. The chamber 4 is fed with plasma via a nozzle 15. The nozzle 15 may advantageously be terminated by one or more injectors serving to make the plasma stream uniform. The vacuum pump 6 also serves to evacuate the plasma to the outside via a pipe 7 provided with filters 8.

The sterilization chamber 4 is referred to as a "post-discharge" chamber since the plasma is not subjected to an electric field therein, being subjected to the field in the enclosure 2. The plasma present in the chamber 4, referred to as a "post-discharge" plasma, that is not subjected to an electric field, thus no longer contains any ultraviolet (UV) radiation, any ions, or any electrons, thereby making it possible to avoid excessively raising the temperature inside the chamber 4, which would damage the articles 10 that are to be sterilized.

The sterilization chamber 4 is in the form of a rectangular parallelepiped, and includes a metal or non-metal instrument carrier 9 for receiving the articles 10 to be sterilized. The sterilization chamber 4 is provided with heater means 11 delivering a temperature that is controlled by a control device 12. These heater means can be constituted, in particular by an electrical resistor or by inductance heater means.

The sterilization chamber 4 is closed on one of its sides by a pivotal door 13.

The chamber 4 is also provided with a reflector 14 and a fan 16 that contributes to making the plasma uniform.

Articles 10 for sterilizing, together with one or more sterilization indicators 17, are introduced into the chamber 4. The sterilization indicators 17 may be placed throughout the chamber 4, and in particular in locations that are difficult to access, such as against its walls or under the articles 10 to be sterilized. In this manner, it is possible to ensure that the entire volume of the sterilization chamber is treated by the nitrogen plasma.

It is also particularly useful to place sterilization indicators 17 on sterilization pockets containing the articles 10 to be sterilized, or inside the articles, in order to ensure that the articles 10 themselves have been in contact with the atoms of nitrogen N.

The pressure that exists inside the sterilization chamber 4 is preferably less than $10^5$ pascals (Pa), so as to facilitate putting atoms of nitrogen N into contact with the articles 10.

Figure 2:
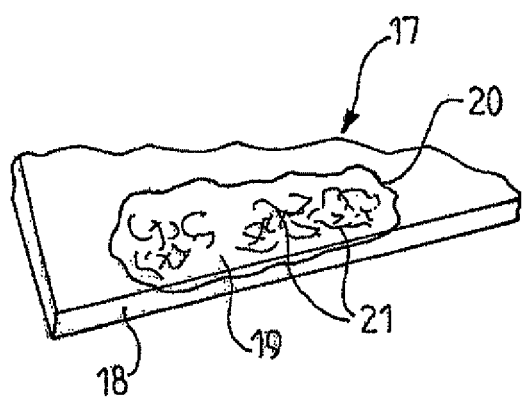
FIG. 2 shows the indicator in a first embodiment of the invention.

FIG. 2 shows a sterilization indicator 17 of the invention.

The sterilization indicator 17 comprises a medium 18 that is impregnated with a dye 19 that diffuses in the medium 18 to form a dye zone 20. A compound 21, in the form of metal fibers, is placed in the medium and in the dye zone 20. As shown in FIG. 2, the fibers are disposed within the dye zone 20, but it is also possible to envisage the fibers being dispersed over the entire medium 18, thus extending beyond the dye zone 20.

Figure 3:
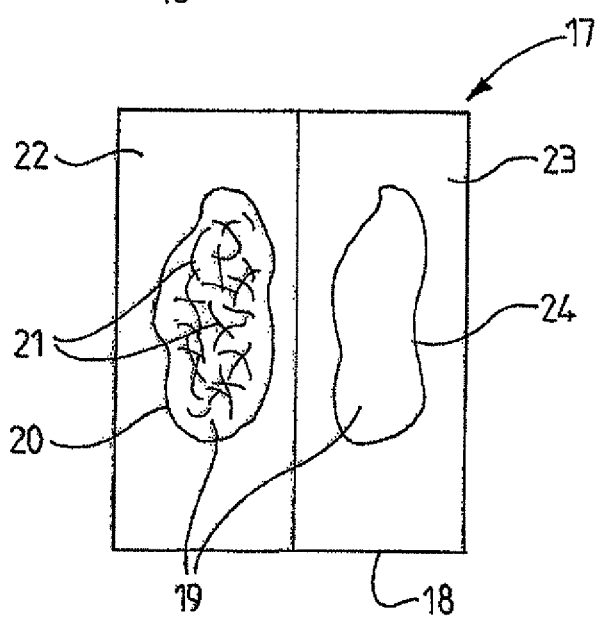
FIG. 3 is a plan view of an indicator in a second embodiment.

FIG. 3 shows a sterilization indicator 17 of the invention in two portions. The indicator 17 comprises a first portion 22 comprising a dye 19 that has diffused in the medium 18 to form a dye zone 20. A compound 21 in the form of metal fibers is disposed in the medium in the dye zone 20.

In the second portion 23 of the indicator 17, which does not include the compound 21, the dye 19 forms a dye zone 24. The two dye zones 20 and 24 are far enough apart for the metal fibers 21 not to be in thermal contact with the dye zone 24 of the second portion 23.

In the two examples below, the parameters of the sterilization process are as follows: the temperature in the sterilization chamber 4 is 60° C., a nitrogen flow rate is delivered at 1 liter per minute (L/min), using nitrogen at a pressure of $6.66 \times 10^2$ Pa (5 Torr), and with an exposure time to the post-discharge plasma of 40 min.

Furthermore, the dye 19 used is the Kromagen magenta 120 screen ink dye.

The color of the dye varies as a function of temperature as follows:

20° C.: pale whitey pink
60° C.: pale pink
70° C.: pink
90° C.: magenta
120° C.: purple With the help of various reference tests, it has been determined that the heating of the metal in the indicators of Examples 1 and 2 needs to bring the dye up to a temperature of 90° C. if the above-indicated parameters are complied with.

EXAMPLE 1

A One-Portion Sterilization Indicator

The medium 18 was constituted by meta-aramid fibers.

The compound 21 was constituted by copper nickel alloy filaments having a diameter of 20 micrometers (μm) as sold under the name Monel® by the supplier Baltec Ltd. One way of fabricating the indicator consists in putting the filaments 21 into contact with the medium 18, and then pouring the dye 19 onto the medium 18, and in allowing it to dry at 20° C. The indicator 17 as made in this way presents a pale whitey pink color.

The indicator 17 was placed in the chamber 4 where it was subjected to the sterilization process.

The dye 19 of the indicator 17 was observed after 1 minute of sterilization. Its color was pale pink, showing that the temperature in the chamber 4 was substantially 60° C.

At the end of the process, the indicator 17 was of a magenta color (dark pink), i.e. it had the desired color.

EXAMPLE 2

A Two-Portion Sterilization Indicator

The medium 18 was constituted by cotton fibers.

One way of fabricating the indicator consists in mixing copper filaments with a diameter of 20 µm with cotton fibers in the first portion 22 of the indicator 17, and then in spreading the dye 19 on the medium 18, both in the first portion 22 and in the second portion 23 so as to form two dye zones 20 and 24, and leaving it to dry at 20° C. The indicator 17 as fabricated in this way presents a pale whitey pink color.

At the end of the process, the dye zone 24 was pale pink, showing that the temperature in the chamber 4 was substantially 60° C. The dye zone 20 was of magenta color (dark pink). The test was thus valid.

Thus, the color of the dye in contact with the metal is determined by taking into account the various parameters that it is desired to use during the sterilization process, such as the concentration of atoms of nitrogen N in the plasma, the duration of the exposure of the articles 10 to the plasma, the temperature that exists inside the sterilization chamber 4, and the volume of the articles 10. The concentration in atoms of nitrogen N can be selected by adjusting the power of the microwave generator 3 and also the flow rate of nitrogen.

The determination of the color of the dye also takes account of the nature of the metal 21, since the heating of the surface of the metal is a function of the nature of the metal, as well as of the quantity of atoms of nitrogen N in contact with the metal 21.

Thus, by means of the indicator 17 of the invention, it is possible to validate two parameters of the sterilization process, namely the quantity of atoms of nitrogen N and the sterilization temperature.

It can be decided to determine the sterility assurance level of the process as a function of the pressure and of the flow rate of nitrogen, of the content in terms of atoms of nitrogen N, of the temperature in the sterilization chamber 4, and of the duration of sterilization. Since the density of atoms of nitrogen N is proportional to the power of the microwave generator 3, at given nitrogen pressure and flow rate, the parameters for verification are temperature, content of atoms of nitrogen N, and duration of the treatment.

The sterilization indicator 17 of the invention is thus particularly suitable for ensuring that the atoms of nitrogen N present in the post-discharge plasma have indeed come into contact with all of the sterilization chamber, as well as with the articles 10 to be sterilized. The indicator 17 also functions with post-discharge plasmas obtained from gas comprising a mixture of $N_2$ with other species, such as the plasmas obtained from $N_2/H_2$ or $Ar/N_2$.

The indicator 17 also functions with atoms of oxygen O present in a post-discharge plasma obtained from a gas including oxygen $O_2$, such as plasmas obtained from $N_2/O_2$ or $Ar/O_2$.

The invention claimed is:

1. A sterilization indicator comprising:
a first portion comprising a compound having at least one metal that is of the heating type when put into contact with atoms of oxygen O and/or nitrogen N, and a first thermochromic dye in thermal contact with the compound, wherein the thermochromic dye changes color due to a rise in temperature; and
a second portion adjacently connected to the first portion, the second portion comprising a second thermochromic dye and not including a compound comprising at least one metal of the heating type when put into contact with atoms of oxygen O and/or nitrogen N,
wherein the metal is selected from the group consisting of copper and alloys thereof.

2. A sterilization device comprising:
a sterilization indicator having
a first portion comprising a compound having at least one metal that is of the heating type when put into contact with atoms of oxygen O and/or nitrogen N, and a first thermochromic dye in thermal contact with the compound, wherein the thermochromic dye changes color due to a rise in temperature, and
a second portion adjacently connected to the first portion, the second portion comprising a second thermochromic dye and not including a compound comprising at least one metal of the heating type when put into contact with atoms of oxygen O and/or nitrogen N;
a plasma generating device that produces plasma from a gas comprising oxygen and/or nitrogen; and
a post-discharge chamber arranged to contact the plasma with the first portion of the sterilization indicator.

3. A method of indicating the presence of atoms of oxygen O and/or nitrogen N in a plasma present in a post-discharge chamber, the method comprising the steps of:
putting a sterilization indicator into contact with the plasma, the sterilization indicator having a first portion comprising a compound having at least one metal that is of the heating type when put into contact with atoms of oxygen O and/or nitrogen N, and a first thermochromic dye in thermal contact with the compound, wherein the thermochromic dye changes color due to a rise in temperature, and a second portion adjacently connected to the first portion, the second portion comprising a second thermochromic dye and not including a compound comprising at least one metal of the heating type when put into contact with atoms of oxygen O and/or nitrogen N, wherein the contact of the sterilization indicator with the plasma causes an exothermic reaction causing a change in color to the first thermochromic dye;
subjecting the post-discharge chamber to a desired quantity of atoms of oxygen O and/or nitrogen N; and then
comparing a final color of the first thermochromic dye of the sterilization indicator with a reference color.

4. A method of indicating: a) the presence of atoms of oxygen O and/or nitrogen N in a plasma present in a post-discharge chamber; and b) a temperature in the post-discharge chamber, comprising the steps:
putting a sterilization indicator into contact with the plasma in the post-discharge chamber, the sterilization indicator having a first portion comprising a compound having at least one metal that is of the heating type when put into contact with atoms of oxygen O and/or nitrogen N, and a first thermochromic dye in thermal contact with the compound, wherein the thermochromic dye changes color due to a rise in temperature, and a second portion comprising a second thermochromic dye coupled to the first portion, and not including a compound comprising at least one metal of the heating type when put into contact with atoms of oxygen O and/or nitrogen N, wherein contact of the first portion of the sterilization indicator with the plasma causes an exothermic reaction causing a change in color to the first thermochromic dye in the first portion and the change in temperature in the post-discharge chamber causes a change in color to the second thermochromic dye of the second portion; and then comparing the color of the second thermochromic dye of the sterilization indicator with a first reference color characteristic of a reference temperature in the chamber; and then comparing the color of the first thermochromic dye of the sterilization indicator with a second referenced color characteristic of a reference quantity of atoms of oxygen O and/or nitrogen N.

5. The sterilization device according to claim 2, wherein the at least one metal of the sterilization indicator is selected from the group consisting of copper, titanium, steels, aluminum, and alloys thereof.

6. The sterilization device according to claim 5, wherein the at least one metal of the sterilization indicator is selected from the group consisting of copper and alloys thereof.

7. The sterilization device according to claim 2, wherein the compound of the sterilization indicator is in the form of a powder, particles, filaments, or fibers.

8. The sterilization device according to claim 2, wherein the compound and the first thermochromic dye of the sterilization indicator are in contact with a medium.

9. The sterilization device according to claim 8, wherein the medium of the sterilization indicator is in the form of a plate or in the form of fibers.

10. The sterilization device according to claim 9, wherein the medium of the sterilization device is selected from the group consisting of cellulose, fabrics, cotton, paper, and blotting paper.

11. The sterilization device according to claim 2, wherein either or both of the first and second thermochromic dyes of the sterilization indicator is an irreversible thermochromic dye.

* * * * *